United States Patent
Abe et al.

(10) Patent No.: US 10,915,987 B2
(45) Date of Patent: Feb. 9, 2021

(54) X-RAY DIAGNOSTIC APPARATUS AND DISPLAY METHOD

(71) Applicant: CANON MEDICAL SYSTEMS CORPORATION, Otawara (JP)

(72) Inventors: Shingo Abe, Nasushiobara (JP); Yusuke Narabu, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 42 days.

(21) Appl. No.: 15/877,861

(22) Filed: Jan. 23, 2018

(65) Prior Publication Data

US 2018/0211363 A1 Jul. 26, 2018

(30) Foreign Application Priority Data

Jan. 23, 2017 (JP) ................................ 2017-009552

(51) Int. Cl.
*G06T 3/40* (2006.01)
*G01T 1/20* (2006.01)
(Continued)

(52) U.S. Cl.
CPC .............. *G06T 3/4038* (2013.01); *A61B 6/06* (2013.01); *A61B 6/40* (2013.01); *A61B 6/4266* (2013.01);
(Continued)

(58) Field of Classification Search
CPC ....... G06T 3/4038; G06T 11/008; A61B 6/06; A61B 6/40; A61B 6/4266; A61B 6/5241; G01T 1/17; G01T 1/2018; G01T 1/2985
See application file for complete search history.

(56) References Cited

U.S. PATENT DOCUMENTS

| | | | | | |
|---|---|---|---|---|---|
| 5,355,309 | A | * | 10/1994 | Eberhard | G01N 23/046 250/208.1 |
| 2006/0002508 | A1 | * | 1/2006 | Yahata | A61B 6/4021 378/19 |
| 2008/0187095 | A1 | * | 8/2008 | Boone | A61B 6/482 378/37 |
| 2010/0215142 | A1 | * | 8/2010 | Dafni | A61B 6/032 378/19 |

(Continued)

FOREIGN PATENT DOCUMENTS

| | | |
|---|---|---|
| JP | H08-215181 A | 8/1996 |
| JP | 2004-073578 A | 3/2004 |

(Continued)

OTHER PUBLICATIONS

Japanese Office Action dated Nov. 10, 2020, issued in Japanese Patent Application No. 2017-009552.

*Primary Examiner* — David P Porta
*Assistant Examiner* — Jeremy S Valentiner
(74) *Attorney, Agent, or Firm* — Oblon, McClelland, Maier & Neustadt, L.L.P.

(57) ABSTRACT

According to an X-ray diagnostic apparatus, an X-ray tube radiates X-rays. An X-ray collimator adjusts an irradiation region of the X-rays. An X-ray detector includes a first detector and a second detector having a smaller detection area than a detection area of the first detector. The X-ray detector is able to detect the X-rays radiated with the first detector and the second detector at the same time. Processing circuitry generates a synthesized image obtained by synthesizing a first X-ray image generated based on an output from the first detector that detected the X-rays radiated in the irradiation region adjusted, and a second X-ray image generated based on an output from the second detector that detected the X-rays radiated in the irradiation region adjusted, the synthesized image having an image size corresponding to an aspect ratio of the irradiation region. The processing circuitry causes a display to display the synthesized image.

17 Claims, 7 Drawing Sheets

(51) Int. Cl.
*G01T 1/17* (2006.01)
*G06T 11/00* (2006.01)
*G21K 1/02* (2006.01)
*A61B 6/00* (2006.01)
*A61B 6/06* (2006.01)
*G01T 1/29* (2006.01)
*G21K 1/04* (2006.01)

(52) U.S. Cl.
CPC .............. *A61B 6/5241* (2013.01); *G01T 1/17* (2013.01); *G01T 1/2018* (2013.01); *G01T 1/2985* (2013.01); *G06T 11/008* (2013.01); *G21K 1/02* (2013.01); *A61B 6/4441* (2013.01); *A61B 6/465* (2013.01); *G06T 2200/32* (2013.01); *G06T 2210/41* (2013.01); *G21K 1/04* (2013.01)

(56) References Cited

U.S. PATENT DOCUMENTS

| | | | |
|---|---|---|---|
| 2010/0266181 A1* | 10/2010 | Oeckl | G01N 23/046 382/131 |
| 2015/0003584 A1 | 1/2015 | Weisfield et al. | |
| 2019/0069859 A1* | 3/2019 | Cao | A61B 6/032 |

FOREIGN PATENT DOCUMENTS

| | | | |
|---|---|---|---|
| JP | 2007-105345 | 4/2007 | |
| JP | 2011-255098 | 12/2011 | |
| JP | 2014-33850 | 2/2014 | |
| JP | 2016-524152 A | 8/2016 | |
| WO | WO-2016137226 A1 * | 9/2016 | A61B 6/461 |

* cited by examiner

X-RAY DIAGNOSTIC APPARATUS AND DISPLAY METHOD

CROSS-REFERENCE TO RELATED APPLICATIONS

This application is based upon and claims the benefit of priority from Japanese Patent Application No. 2017-9552, filed on Jan. 23, 2017; the entire contents of which are incorporated herein by reference.

FIELD

Embodiments described herein relate generally to an X-ray diagnostic apparatus and a display method.

BACKGROUND

In inspection using an X-ray diagnostic apparatus in the related art, there is a case of observing a region of interest with high-resolution while observing a wide region of a subject in bird's-eye view. In recent years, as the X-ray diagnostic apparatus used for such inspection, there is known an X-ray diagnostic apparatus including a detector that includes both of a first detector including a large visual field part employing a thin film transistor (TFT) array and a second detector the visual field of which is smaller than that of the first detector and the pixel pitch of which is fine, the second detector using a complementary metal oxide semiconductor (CMOS).

In such an X-ray diagnostic apparatus, for example, the first detector and the second detector are used in a switching manner in accordance with use to display one of a first X-ray image based on a signal output from the first detector and a second X-ray image based on a signal output from the second detector.

DETAILED DESCRIPTION

According to an embodiment, an X-ray diagnostic apparatus includes an X-ray tube, an X-ray collimator, an X-ray detector and processing circuitry. The X-ray tube is configured to radiate X-rays. The X-ray collimator is configured to adjust an irradiation region of the X-rays radiated by the X-ray tube. The X-ray detector includes a first detector and a second detector having a smaller detection area than a detection area of the first detector. The X-ray detector is configured to be able to detect the X-rays radiated by the X-ray tube with the first detector and the second detector at the same time. The processing circuitry is configured to generate a synthesized image obtained by synthesizing a first X-ray image generated based on an output from the first detector that detected the X-rays radiated in the irradiation region adjusted by the X-ray collimator, and a second X-ray image generated based on an output from the second detector that detected the X-rays radiated in the irradiation region adjusted, the synthesized image having an image size corresponding to an aspect ratio of the irradiation region. The processing circuitry is configured to cause a display to display the synthesized image.

The following describes embodiments of an X-ray diagnostic apparatus and a display method in detail with reference to the attached drawings. The X-ray diagnostic apparatus and the display method according to the present application are not limited to the following embodiments.

First Embodiment

Figure 1:
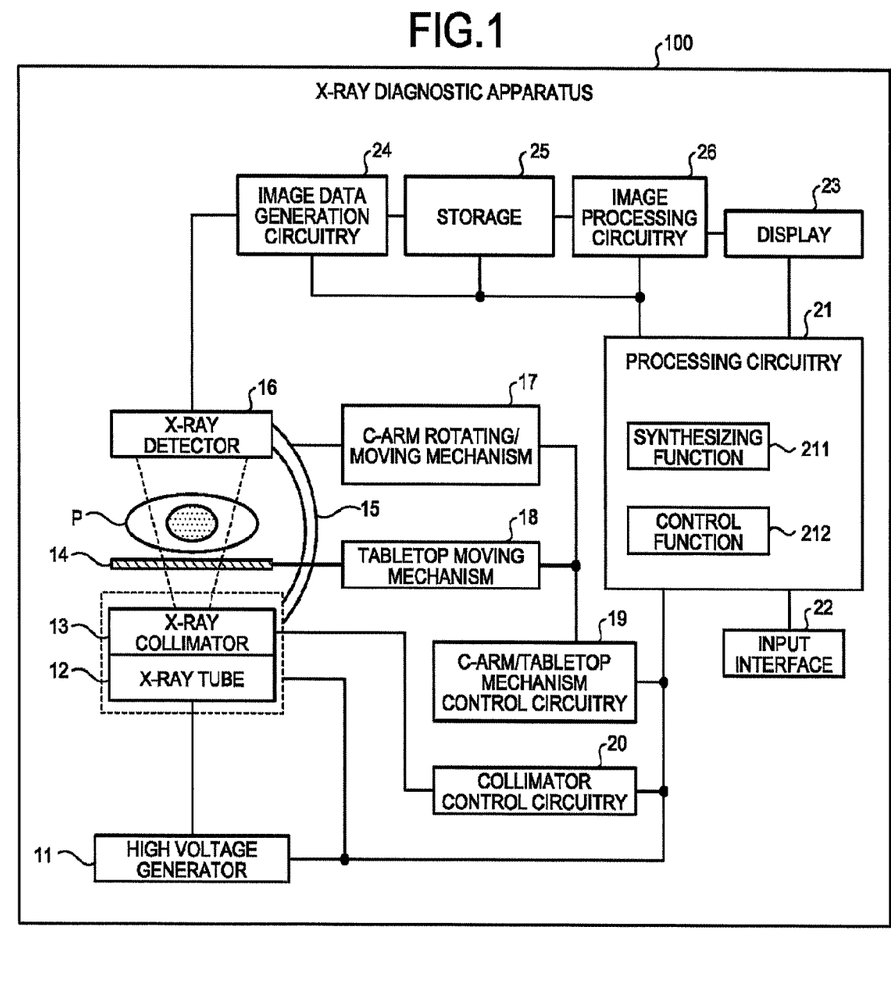
FIG. 1 is a diagram illustrating a configuration example of an X-ray diagnostic apparatus according to a first embodiment.

First, the following describes the entire structure of an X-ray diagnostic apparatus according to a first embodiment. FIG. 1 is a diagram illustrating a configuration example of an X-ray diagnostic apparatus 100 according to the first embodiment. As illustrated in FIG. 1, the X-ray diagnostic apparatus 100 according to the first embodiment includes a high voltage generator 11, an X-ray tube 12, an X-ray collimator 13, a tabletop 14, a C-arm 15, an X-ray detector 16, a C-arm rotating/moving mechanism 17, a tabletop moving mechanism 18, C-arm/tabletop mechanism control circuitry 19, collimator control circuitry 20, processing circuitry 21, an input interface 22, a display 23, image data generation circuitry 24, a storage 25, and image processing circuitry 26.

In the X-ray diagnostic apparatus 100 illustrated in FIG. 1, each processing function is stored in the storage 25 as a computer-executable program. Each of the C-arm/tabletop mechanism control circuitry 19, the collimator control circuitry 20, the processing circuitry 21, the image data generation circuitry 24, and the image processing circuitry 26 is a processor that implements a function corresponding to each program by reading out and executing the program from the storage 25. In other words, each circuitry that has read out each program has a function corresponding to the program that has been read out.

The word "processor" used in the above description means, for example, a central processing unit (CPU), a graphics processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). The processor reads out and executes the program stored in the storage to implement the function. Instead of storing the program in the storage, the program may be directly embedded in the circuit of the processor. In this case, the processor implements the function by reading out and executing the program embedded in the circuit. Each processor according to the embodiment is not necessarily configured as a single circuit. Alternatively, a plurality of independent circuits may be combined to be one processor to implement the function.

The high voltage generator 11 generates high voltage under control by the processing circuitry 21, and supplies the generated high voltage to the X-ray tube 12. The X-ray tube 12 generates X-rays using the high voltage supplied from the high voltage generator 11.

The X-ray collimator 13 narrows the X-rays generated by the X-ray tube 12 to be selectively emitted to a region of interest of a subject P under control by the collimator control circuitry 20. For example, the X-ray collimator 13 includes four slidable collimator blades. The X-ray collimator 13 causes these collimator blades to slide to narrow the X-rays generated by the X-ray tube 12 to be emitted to the subject P under control by the collimator control circuitry 20. The X-ray collimator 13 includes an additional filter for adjusting radiation quality. For example, the additional filter is set in accordance with inspection. The tabletop 14 is a bed on which the subject P is placed, and is arranged on a couch (not illustrated). The subject P is not included in the X-ray diagnostic apparatus 100.

Figure 2A:
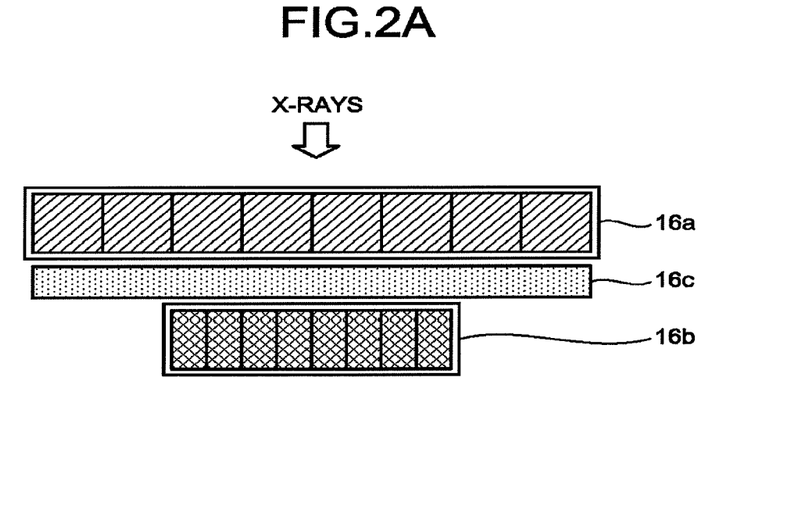
FIG. 2A is a diagram illustrating a configuration example of an X-ray detector according to the first embodiment.
Figure 2B:
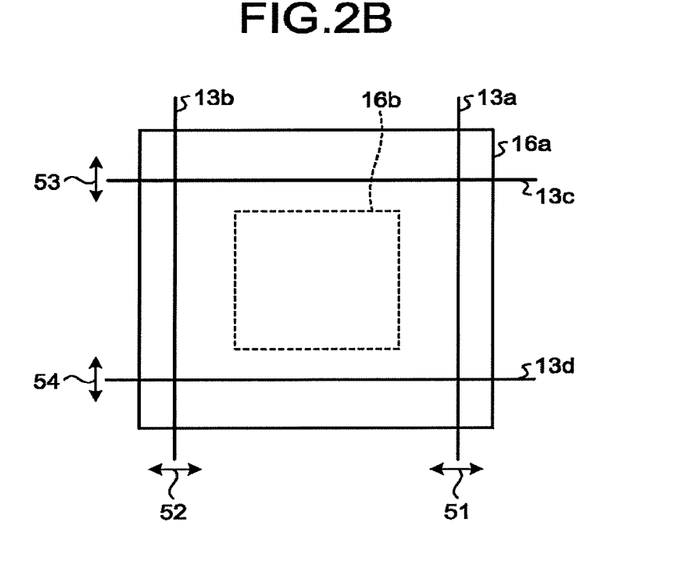
FIG. 2B is a diagram illustrating a configuration example of the X-ray detector according to the first embodiment.

The X-ray detector 16 detects the X-rays transmitted through the subject P. For example, the X-ray detector 16 includes detection elements arranged in a matrix. Each detection element converts the X-rays transmitted through the subject P into electric signals to be accumulated, and transmits the accumulated electric signals to the image data generation circuitry 24. The X-ray detector 16 according to the present embodiment includes two detectors having different pixel pitches. FIGS. 2A and 2B are diagrams illustrating a configuration example of the X-ray detector 16 according to the first embodiment. FIG. 2A illustrates a vertical cross-sectional view of the X-ray detector 16. FIG. 2B illustrates a top view of the X-ray detector 16.

For example, as illustrated in FIG. 2A, the X-ray detector 16 includes a first photodetector 16a, a second photodetector 16b, and a scintillator 16c. The first detector is constituted of the first photodetector 16a and the scintillator 16c, and the second detector is constituted of the second photodetector 16b and the scintillator 16c.

The scintillator 16c converts the X-rays emitted from the X-ray tube 12 into light. The first photodetector 16a includes, for example, a two-dimensional image sensor employing a thin film transistor (TFT) array made of amorphous silicon, and detects the light converted by the scintillator 16c to output an electric signal. The second photodetector 16b includes, for example, a two-dimensional image sensor employing a complementary metal oxide semiconductor (CMOS) transistor, and detects the light converted by the scintillator 16c to output the electric signal. Hereinafter, the electric signal output by the first photodetector 16a is referred to as a first electric signal, and the electric signal output by the second photodetector 16b is referred to as a second electric signal.

In this way, the scintillator 16c is shared by the first photodetector 16a and the second photodetector 16b. In other words, the X-ray detector 16 includes the scintillator 16c that converts the X-rays emitted from the X-ray tube 12 into light, and the first photodetector 16a and the second photodetector 16b that share the scintillator 16c and detect the light converted by the scintillator 16c to output the electric signal. Each of the first photodetector 16a and the second photodetector 16b outputs the electric signal obtained by detecting the light converted by the scintillator 16c at the same time.

As illustrated in FIG. 2A, the first photodetector 16a and the second photodetector 16b include a plurality of elements as constituent units of pixels. Each of the elements converts a fluorescent image obtained through X-ray incidence into an electric signal to be accumulated in a photo diode (PD). FIG. 2A exemplifies a case in which the first photodetector 16a includes eight elements in one column and the second photodetector 16b includes eight elements in one column.

The pixel pitch of the elements of the second photodetector 16b is finer than the pixel pitch of the elements of the first photodetector 16a. In the example illustrated in FIG. 2A, the pixel pitch of each of the elements of the first photodetector 16a corresponds to the pixel pitch of two elements of the second photodetector 16b. That is, on an XY-plane of the X-ray detector 16, one element of the first photodetector 16a corresponds to four elements of the second photodetector 16b. Thus, resolution of the second photodetector 16b is higher than that of the first photodetector 16a.

As illustrated in FIG. 2B, a visual field size of the first photodetector 16a is larger than that of the second photodetector 16b. That is, as illustrated in FIG. 2B, the second photodetector 16b has a size to be overlapped with part of a detection area of the first photodetector 16a. Thus, the second photodetector 16b collects high-resolution X-ray image data in the region overlapping with the first photodetector 16a. In the X-ray diagnostic apparatus 100, the X-ray collimator 13 includes four collimator blades, and these collimator blades are slid under control by the collimator control circuitry 20. For example, in the X-ray diagnostic apparatus 100, as illustrated in FIG. 2B, the X-ray collimator 13 includes collimator blades 13a to 13d.

The collimator blade 13a is arranged in parallel with one side of the first photodetector 16a and the second photodetector 16b, and is slid in a direction of a double-headed arrow 51 to adjust an X-ray irradiation region. The collimator blade 13b is arranged in parallel with one side of the first photodetector 16a and the second photodetector 16b and in parallel with the collimator blade 13a, and is slid in a direction of a double-headed arrow 52 to adjust the X-ray irradiation region. The collimator blade 13c is arranged in parallel with one side of the first photodetector 16a and the second photodetector 16b and in a direction orthogonal to the collimator blade 13a and the collimator blade 13b, and is slid in a direction of a double-headed arrow 53 to adjust the X-ray irradiation region. The collimator blade 13d is arranged in parallel with one side of the first photodetector 16a and the second photodetector 16b and in parallel with the collimator blade 13c, and is slid in a direction of a double-headed arrow 54 to adjust the X-ray irradiation region.

Detection sensitivity of the first photodetector 16a is higher than that of the second photodetector 16b. In the second photodetector 16b employing the CMOS, a maximum X-ray incident amount tends to be smaller than that of the first photodetector 16a employing the amorphous silicon. Thus, in the second photodetector 16b, a dynamic range is lowered in a case of emitting high-dose of X-rays and collecting X-ray image data having a high signal to noise (S/N) ratio.

In the second photodetector 16b, an amount of residual components of the electric signal is smaller than that of the first photodetector 16a. In the first photodetector 16a, a generated electric charge is trapped at a trap level within the photo diode. On the other hand, in the second photodetector 16b, the electric charge generated in the photo diode is less trapped in the CMOS due to a characteristic thereof.

Returning to FIG. 1, the C-arm 15 holds the X-ray tube 12, the X-ray collimator 13, and the X-ray detector 16. The C-arm 15 rotates around the subject P lying on the tabletop 14 at high speed like a propeller by a motor arranged in a supporting part (not illustrated). The C-arm 15 is supported to be rotatable about each of XYZ-axes, that is, three axes orthogonal to each other, and individually rotates about each axis by a driving unit (not illustrated). The X-ray tube 12 and the X-ray collimator 13 are arranged to be opposed to the X-ray detector 16 across the subject P with the C-arm 15. FIG. 1 exemplifies a case in which the X-ray diagnostic apparatus 100 is a single plane, but the embodiment is not limited thereto. Alternatively, the X-ray diagnostic apparatus 100 may be a biplane.

The C-arm rotating/moving mechanism 17 is a mechanism for rotating and moving the C-arm 15. The C-arm rotating/moving mechanism 17 can also change a source image receptor distance (SID) as a distance between the X-ray tube 12 and the X-ray detector 16. The C-arm rotating/moving mechanism 17 can also rotate the X-ray detector 16 held by the C-arm 15. The tabletop moving mechanism 18 is a mechanism for moving the tabletop 14.

The C-arm/tabletop mechanism control circuitry 19 adjusts rotation or movement of the C-arm 15, and movement of the tabletop 14 by controlling the C-arm rotating/moving mechanism 17 and the tabletop moving mechanism 18 under control by the processing circuitry 21. For example, the C-arm/tabletop mechanism control circuitry 19 controls rotatography for collecting projection data at a predetermined frame rate while rotating the C-arm 15 under control by the processing circuitry 21. The collimator control circuitry 20 controls an irradiation region of X-rays emitted to the subject P by adjusting an aperture of the collimator blade included in the X-ray collimator 13 under control by the processing circuitry 21.

The image data generation circuitry 24 generates projection data using the electric signal converted from the X-ray by the X-ray detector 16, and stores the generated projection data in the storage 25. Specifically, the image data generation circuitry 24 generates first projection data from the first electric signal output by the first photodetector 16a, generates second projection data from the second electric signal output by the second photodetector 16b, and stores each piece of the generated projection data in the storage 25. For example, the image data generation circuitry 24 performs current/voltage conversion, analog (A)/digital (D) conversion, and parallel/serial conversion on the first electric signal and the second electric signal received from the X-ray detector 16, and generates the first projection data based on the first electric signal and the second projection data based on the second electric signal. The image data generation circuitry 24 stores the generated first projection data and second projection data in the storage 25.

The storage 25 receives and stores the projection data generated by the image data generation circuitry 24. For example, the storage 25 stores the first projection data based on the first electric signal and the second projection data based on the second electric signal. The storage 25 also stores volume data and an X-ray image generated by the image processing circuitry 26. The storage 25 stores a synthesized image synthesized by the processing circuitry 21. Details about the synthesized image will be described later. The storage 25 stores the programs corresponding to various functions that are read out and executed by the respective circuitry illustrated in FIG. 1. By way of example, the storage 25 stores the program corresponding to a synthesizing function 211 and the program corresponding to a control function 212 that are read out and executed by the processing circuitry 21.

The image processing circuitry 26 generates an X-ray image by performing various pieces of image processing on the projection data stored in the storage 25 under control by the processing circuitry 21 described later. Alternatively, the image processing circuitry 26 directly acquires the projection data from the image data generation circuitry 24 under control by the processing circuitry 21 described later, and generates the X-ray image by performing various pieces of image processing on the acquired projection data. For example, the image processing circuitry 26 generates the first X-ray image by performing image processing on the first projection data based on the first electric signal. The image processing circuitry 26 generates the second X-ray image by performing image processing on the second projection data based on the second electric signal. The image processing circuitry 26 can store the X-ray image after image processing in the storage 25. For example, the image processing circuitry 26 can perform various pieces of processing using an image processing filter such as a moving-average (smoothing) filter, a Gaussian filter, a median filter, a recursive filter, and a band-pass filter.

The image processing circuitry 26 reconstructs reconstruction data (volume data) from the projection data collected through rotatography. For example, the image processing circuitry 26 reconstructs first reconstruction data from the first projection data collected through rotatography. The image processing circuitry 26 reconstructs second reconstruction data from the second projection data collected through rotatography. The image processing circuitry 26 stores the reconstructed volume data in the storage 25. The image processing circuitry 26 generates a three-dimensional image from the volume data. For example, the image processing circuitry 26 generates a volume rendering image and a multi planar reconstruction (MPR) image from the volume data. The image processing circuitry 26 then stores the generated three-dimensional image in the storage 25.

The input interface 22 is implemented by a trackball, a switch button, a mouse, a keyboard, and the like for performing setting for a predetermined region (for example, a noticed region such as a region of interest), and a foot switch for emitting X-rays, for example. The input interface 22 is connected to the processing circuitry 21, and converts an input operation received from an operator into the electric signal to be output to the processing circuitry 21. The display 23 displays a graphical user interface (GUI) for receiving an instruction from the operator, various images generated by the image processing circuitry 26, and a synthesized image synthesized by the processing circuitry 21.

The processing circuitry 21 controls the operation of the entire X-ray diagnostic apparatus 100. Specifically, the processing circuitry 21 reads out, from the storage 25, the program corresponding to the control function 212 for controlling the entire device to be executed to perform various pieces of processing. For example, the control function 212 controls the high voltage generator 11 in accordance with an instruction from the operator transferred from the input interface 22 and adjusts voltage to be supplied to the X-ray tube 12 to control ON/OFF and an amount of X-rays to be emitted to the subject P. For example, the control function 212 controls the C-arm/tabletop mechanism control circuitry 19 in accordance with the instruction from the operator, and adjusts rotation or movement of the C-arm 15, and movement of the tabletop 14. For example, the control function 212 controls the collimator control circuitry 20 in accordance with the instruction from the operator and adjusts apertures of the collimator blades 13a to 13d included in the X-ray collimator 13 to control the irradiation region of the X-rays emitted to the subject P.

The control function 212 controls image data generation processing performed by the image data generation circuitry 24, image processing performed by the image processing circuitry 26, analysis processing, or the like in accordance with the instruction from the operator. The control function 212 controls the display 23 to display a GUI for receiving the instruction from the operator, an image stored in the storage 25, and the like.

As illustrated in FIG. 1, the processing circuitry 21 according to the first embodiment executes the synthesizing function 211 in addition to the control function 212 described above. Details about the synthesizing function 211 will be described later. The processing circuitry 21 is an example of processing circuitry according to claims.

The entire structure of the X-ray diagnostic apparatus 100 has been described above. With this configuration, the X-ray diagnostic apparatus 100 according to the present embodiment enables efficiency of inspection to be improved. Specifically, the X-ray diagnostic apparatus 100 enables the X-ray image of a wide region to be observed, and enables a more noticed region to be observed as a high-definition X-ray image by compensating for a region other than a region of a high-definition second X-ray image collected by the second photodetector 16b with the first X-ray image collected by the first photodetector 16a in collecting the X-ray image using the first photodetector 16a having a large visual field size and the second photodetector 16b with high resolution (high definition).

For example, in inspection using the X-ray detector 16 illustrated in FIG. 2B, there may be a case in which a wide region of the subject is first observed in bird's-eye view through the first X-ray image of a wide region collected by the first photodetector 16a, and a region of interest is observed with high-resolution through the high-definition second X-ray image collected by the second photodetector 16b. By way of example, in a case of giving coil embolization treatment for a cerebral aneurysm, the first X-ray image of a wide region is observed when a catheter is inserted from an artery of a groin to be guided to a cerebral artery, and the high-definition second X-ray image is observed when the cerebral aneurysm is embolized with a coil.

The detection area of the high-resolution second photodetector 16b is small, so that the region of interest does not entirely fall within the detection area in some cases. In this case, typically, the first X-ray image of a wide region (the X-ray image photographed in the detection area of the first photodetector 16a) and the high-definition second X-ray image (the X-ray image photographed in the detection area of the second photodetector 16b) are alternately checked. However, it is complicated to alternately check the first X-ray image of a wide region and the high-definition second X-ray image, and there may be the problem that the X-rays are emitted to an unnecessarily wide region and radiation exposure may be increased.

The X-ray diagnostic apparatus 100 then partially widens a photographing range so as to accommodate the entire region of interest in photographing the high-definition second X-ray image, and synthesizes the first image photographed by the first photodetector 16a and the second X-ray image photographed by the second photodetector 16b to be displayed. Accordingly, all regions of interest can be displayed at the same time, and efficiency of inspection can be improved. Additionally, increase in radiation exposure can be reduced. The following describes an example of processing performed by the X-ray diagnostic apparatus 100 according to the first embodiment.

The synthesizing function 211 according to the first embodiment generates a synthesized image obtained by synthesizing the first X-ray image generated from the electric signal output from the first photodetector 16a based on the X-rays emitted in the irradiation region after being adjusted by the X-ray collimator 13 and the second X-ray image generated from the electric signal output from the second photodetector 16b based on the X-rays emitted in the irradiation region after being adjusted while matching image sizes thereof.

Figure 3:
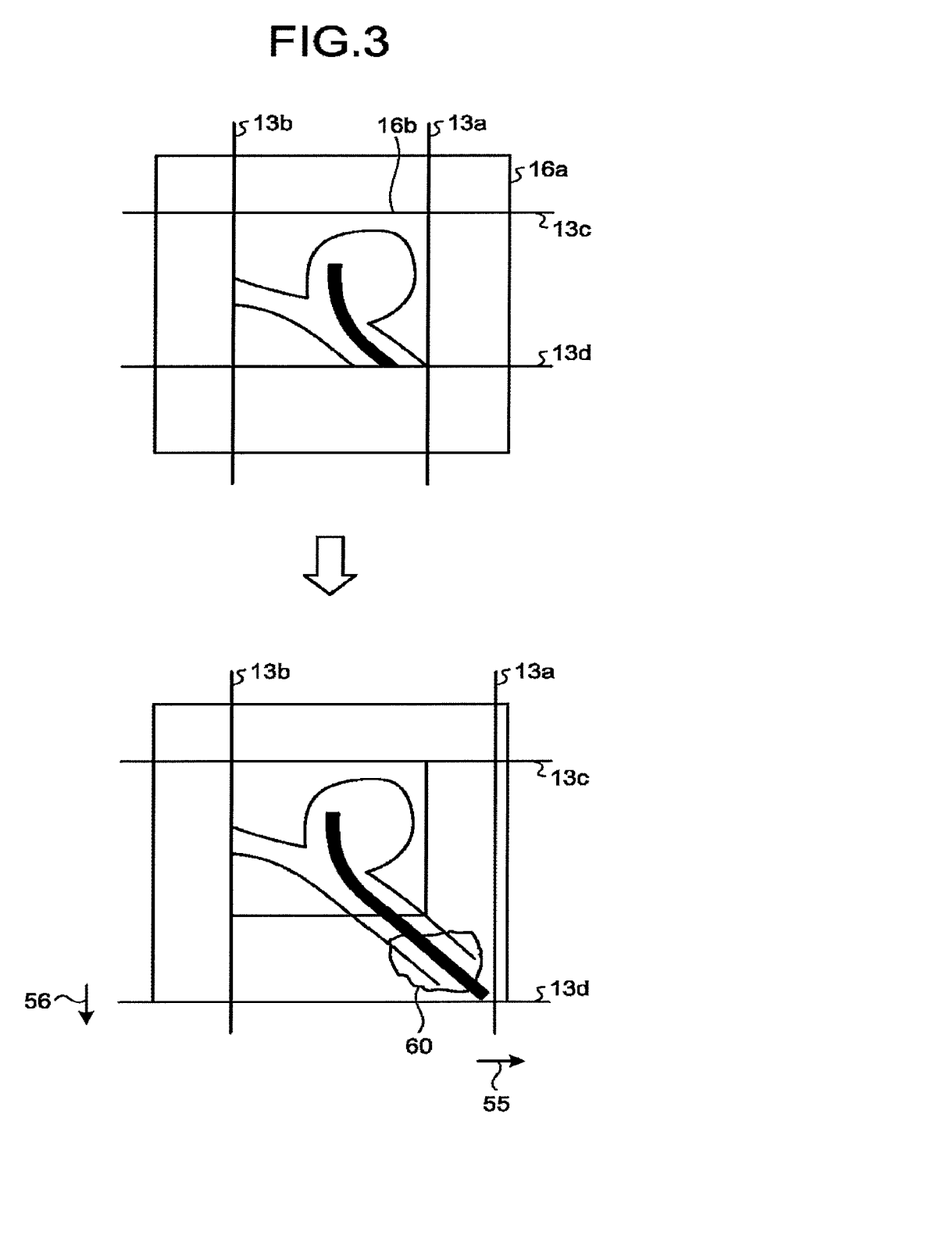
FIG. 3 is a diagram illustrating an example of operation of designating an X-ray irradiation region according to the first embodiment.

First, in the X-ray diagnostic apparatus 100, an instruction for adjusting the X-ray irradiation region is received via the input interface 22. That is, the input interface 22 receives the operation of designating the X-ray irradiation region with the collimator blades 13a to 13d of the X-ray collimator 13. FIG. 3 is a diagram illustrating an example of the operation of designating the X-ray irradiation region according to the first embodiment. For example, the input interface 22 receives an operation of sliding the collimator blades 13a to 13d illustrated in the upper diagram of FIG. 3. The operation of designating the X-ray irradiation region can be executed through an optional operation. For example, the control function 212 causes the display 23 to display a perspective image collected by the second photodetector 16b and a GUI for moving the collimator blades 13a to 13d, and the input interface 22 receives the operation of sliding the collimator blades 13a to 13d.

By way of example, as illustrated in the upper diagram of FIG. 3, the control function 212 causes the GUI to be displayed, the GUI indicating the collimator blades 13a to 13d along respective sides of the high-definition X-ray image (perspective image) collected by the second photodetector 16b.

The input interface 22 receives a slide operation for the collimator blades 13a to 13d displayed along the perspective image. For example, as illustrated in a lower diagram of FIG. 3, the input interface 22 receives an operation of sliding the collimator blade 13a in a direction of an arrow 55 and an operation of sliding the collimator blade 13d in a direction of an arrow 56. Accordingly, for example, an X-ray image including a region 60 and the like other than the second X-ray image can be collected.

Accordingly, for example, an X-ray image including a region 60 and the like other than the second X-ray image can be collected. That is, in the X-ray diagnostic apparatus 100, the image data generation circuitry 24 generates the second projection data from the second electric signal detected in the detection area of the second photodetector 16b, and the image processing circuitry 26 generates the second X-ray image from the second projection data. In the X-ray diagnostic apparatus 100, at the same time, the image data generation circuitry 24 generates the first projection data from the first electric signal detected in the region surrounded by the collimator blades 13a to 13d, and the image processing circuitry 26 generates the first X-ray image from the first projection data.

The synthesizing function 211 generates a synthesized image obtained by synthesizing the first X-ray image and the second X-ray image generated by the image processing circuitry 26. Specifically, the synthesizing function 211 generates the synthesized image obtained by synthesizing the first X-ray image and the second X-ray image while matching the image sizes thereof. As described above, the first photodetector 16a and the second photodetector 16b in the X-ray detector 16 have different pixel pitches (resolution). Thus, when they are simply synthesized, the image sizes are mismatched. Thus, the synthesizing function 211 adjusts the image sizes of the first X-ray image and the second X-ray image based on the pixel pitch of the first photodetector 16a and the pixel pitch of the second photodetector 16b. That is, the synthesizing function 211 adjusts the image sizes of the first X-ray image and the second X-ray image so that the subject in the first X-ray image and the subject in the second X-ray image are displayed in the same ratio when being displayed on the display 23.

Figure 4:
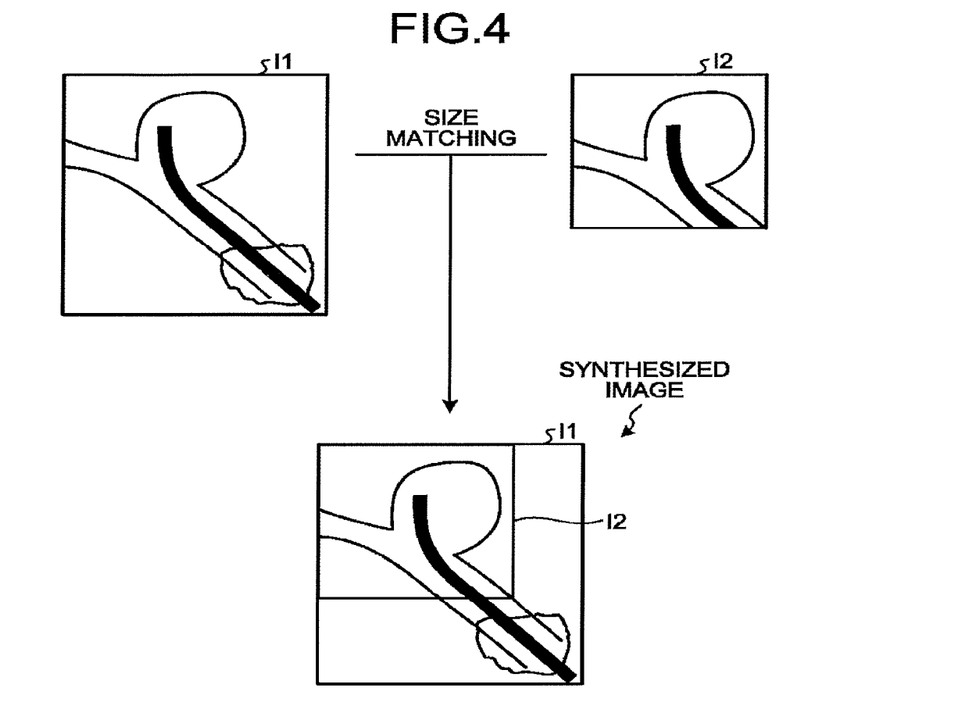
FIG. 4 is a diagram for explaining an example of processing performed by a synthesizing function according to the first embodiment.
Figure 5:
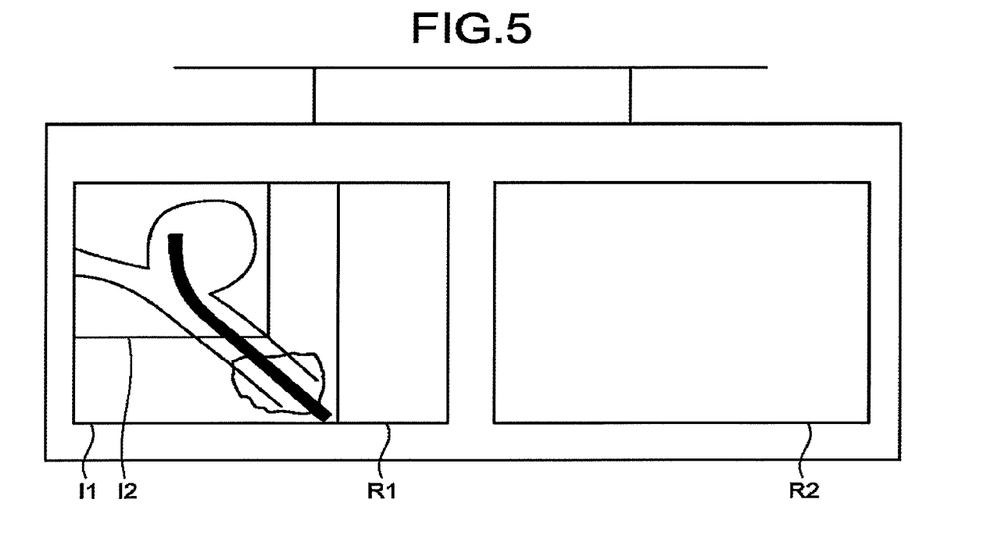
FIG. 5 is a diagram for explaining an example of processing performed by the synthesizing function according to the first embodiment.

FIGS. 4 and 5 are diagrams for explaining an example of processing performed by the synthesizing function 211 according to the first embodiment. For example, as illustrated in FIG. 4, when the image processing circuitry 26 generates a first X-ray image I1 and a second X-ray image I2, the synthesizing function 211 generates the synthesized image in which the subject in the first X-ray image and the subject in the second X-ray image are displayed in the same ratio.

The synthesizing function 211 determines a side serving as a reference of the image size of the synthesized image in accordance with an aspect ratio of the X-ray irradiation region, and changes the image sizes of the first X-ray image I1 and the second X-ray image I2 in accordance with a length of the determined side. That is, the synthesizing function 211 determines the image sizes based on the X-ray irradiation region received via the input interface 22. In this case, first, the synthesizing function 211 acquires positional information of the collimator blades 13a to 13d that are slidingly moved by being controlled by the collimator control circuitry 20, and calculates the X-ray irradiation region based on the acquired positional information. For example, the synthesizing function 211 calculates the X-ray irradiation region surrounded by the collimator blades based on the positional information of the collimator blades 13a to 13d in the lower diagram of FIG. 3.

The synthesizing function 211 determines a side serving as a reference of the image size in the calculated X-ray irradiation region. Specifically, the synthesizing function 211 determines a long side of the X-ray irradiation region to be a side serving as a reference of the image size. For example, the synthesizing function 211 determines, to be a side serving as a reference of the image size, the long side of the X-ray irradiation region (a side in a vertical direction in the drawing) illustrated as a rectangle in FIG. 3.

The synthesizing function 211 then changes the image sizes of the first X-ray image I1 and the second X-ray image I2 so that the length of the side serving as a reference of the image size of the synthesized image is matched with the length of a corresponding side of a display region of the synthesized image on the display 23. For example, as illustrated in FIG. 5, when the display 23 includes two displays including a first display having a display region R1 and a second display having a display region R2, and causes the first display to display the synthesized image, the synthesizing function 211 adjusts the image size so that the size of the synthesized image is matched with the display region of the synthesized image in a display region R1 of the first display.

For example, in a case of displaying the synthesized image in the entire display region R1 of the first display, the synthesizing function 211 changes the image size so that the length of the side serving as a reference is matched with a corresponding side of the display region R1. That is, the synthesizing function 211 changes the image size of the synthesized image so that the length of the long side of the synthesized image (a side in the vertical direction in the drawing) is matched with the length of a corresponding side of the display region R1 (a side in the vertical direction in the drawing).

For example, the synthesizing function 211 magnifies the first X-ray image I1 as an image corresponding to the side serving as a reference to be displayed being matched with upper and lower sides of the display region R1. That is, the synthesizing function 211 changes the image size of the first X-ray image I1 so that the long side of the first X-ray image I1 is displayed being matched with the upper and lower sides of the display region R1. That is, the synthesizing function 211 changes the image size of the first X-ray image I1 so that a pixel on the long side of the first X-ray image I1 is assigned to a pixel in the vertical direction of the display region R1 of the display 23.

The synthesizing function 211 then changes the image size of the second X-ray image I2 so that the subject in the second X-ray image I2 and the subject in the magnified first X-ray image I1 are displayed in the same ratio. That is, the synthesizing function 211 assigns a pixel in the second X-ray image I2 to a pixel in the display region R1 so that the ratio of the subject becomes the same as the ratio of the subject in the magnified first X-ray image I1.

Returning to FIG. 1, the control function 212 causes the display 23 to display the synthesized image. For example, the control function 212 causes the synthesized image of the first X-ray image I1 and the second X-ray image I2 to be displayed in the display region R1 of the first display of the display 23. Accordingly, the observer can observe the entire region of interest at the same time, and the efficiency of inspection can be improved.

In the above example, exemplified is a case in which one first X-ray image I1 and one second X-ray image I2 are collected to be synthesized. Also in a case of a moving image such as a perspective image, the synthesized image is similarly generated as described above. That is, the synthesizing function 211 generates a plurality of synthesized images from a plurality of first X-ray images I1 collected at a first frame rate and a plurality of second X-ray images I2 collected at a second frame rate.

When the first frame rate is the same as the second frame rate, the synthesizing function 211 sequentially generates the synthesized image with the first X-ray image I1 and the second X-ray image I2 that are collected at the same time. On the other hand, when the first frame rate is different from the second frame rate, the synthesizing function 211 generates the synthesized image in accordance with a higher one thereof. By way of example, when the second frame rate is twice the first frame rate, the synthesizing function 211 assigns the same first X-ray image I1 to successive two frames in the second X-ray image I2 that is sequentially collected to generate the synthesized image. That is, the synthesizing function 211 sequentially assigns one frame of the first X-ray image I1 that is sequentially collected for every two successive frames in the second X-ray image I2 that is sequentially collected, and sequentially generates the synthesized image. The control function 212 causes a plurality of synthesized images that are sequentially generated to be displayed in the display region R1 of the display 23 in a time series manner to display a moving image.

In the embodiments described above, exemplified is a case in which the long side of the X-ray irradiation region is along the vertical direction. However, the embodiment is not limited thereto. For example, when the long side of the X-ray irradiation region is along a horizontal direction, the side serving as a reference of the image size becomes a side along the horizontal direction.

Figure 6:
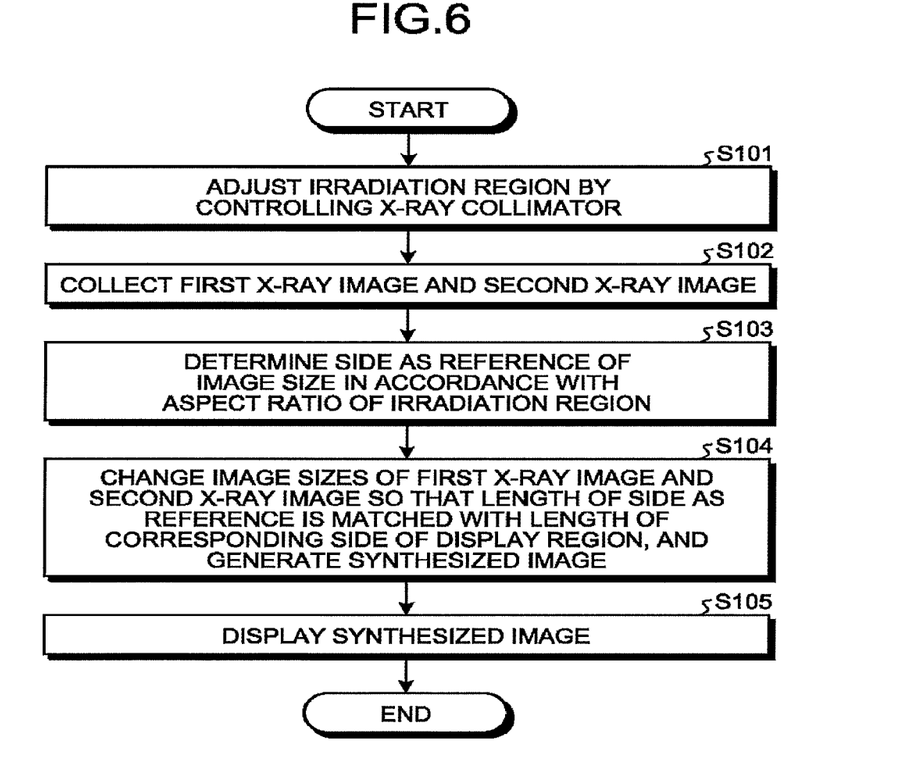
FIG. 6 is a flowchart illustrating a processing procedure of the X-ray diagnostic apparatus according to the first embodiment.

Next, the following describes processing performed by the X-ray diagnostic apparatus 100 according to the first embodiment with reference to FIG. 6. FIG. 6 is a flowchart illustrating a processing procedure of the X-ray diagnostic apparatus 100 according to the first embodiment. Steps S101, S102, and S105 illustrated in FIG. 6 are steps at which the processing circuitry 21 reads out, from the storage 25, the program corresponding to the control function 212 to be executed. Steps S103 and S104 are steps at which the processing circuitry 21 reads out, from the storage 25, the program corresponding to the synthesizing function 211 to be executed.

At Step S101, the processing circuitry 21 controls the X-ray collimator 13 to adjust the X-ray irradiation region. At Step S102, the processing circuitry 21 collects the first X-ray image and the second X-ray image. At Step S103, the processing circuitry 21 determines the side serving as a reference of the image size in accordance with the aspect ratio of the X-ray irradiation region.

At Step S104, the processing circuitry 21 changes the image sizes of the first X-ray image and the second X-ray image so that the length of the side serving as a reference is matched with the length of a corresponding side of the display region, and generates the synthesized image. At Step S105, the processing circuitry 21 causes the display 23 to display the generated synthesized image.

As described above, according to the first embodiment, the X-ray collimator 13 adjusts the irradiation region of the X-rays generated by the X-ray tube 12. The X-ray detector 16 includes the scintillator 16c that converts the X-rays emitted from the X-ray tube 12 into light, and the first photodetector 16a and the second photodetector 16b that share the scintillator 16c and detect the light converted by the scintillator 16c to output the electric signal. The synthesizing function 211 generates the synthesized image obtained by synthesizing the first X-ray image generated from the electric signal output from the first photodetector 16a based on the X-rays emitted in the irradiation region after adjustment by the X-ray collimator 13, and the second X-ray image generated from the electric signal output from the second photodetector 16b based on the X-rays emitted in the irradiation region after adjustment while matching the image sizes thereof with each other. The control function 212 causes the display 23 to display the synthesized image. Thus, the X-ray diagnostic apparatus 100 according to the first embodiment can cause the X-ray image including the entire region of interest to be displayed, and can improve efficiency of inspection. The X-ray diagnostic apparatus 100 according to the first embodiment can suppress increase in radiation exposure by emitting the X-rays only to the region of interest.

According to the first embodiment, the synthesizing function 211 determines the side serving as a reference of the image size of the synthesized image in accordance with the aspect ratio of the irradiation region, and changes the image size of the first X-ray image and the second X-ray image in accordance with the length of the determined side. Accordingly, the X-ray diagnostic apparatus 100 according to the first embodiment enables the synthesized image to be generated considering a display size.

According to the first embodiment, the synthesizing function 211 determines the long side of the irradiation region to be the side serving as a reference of the image size. Accordingly, the X-ray diagnostic apparatus 100 according to the first embodiment enables the image size to be determined considering a maximum size of the X-ray image.

According to the first embodiment, the synthesizing function 211 changes the image sizes of the first X-ray image and the second X-ray image so that the length of the side serving as a reference of the image size of the synthesized image is matched with the length of a corresponding side of the display region of the synthesized image on the display 23. Accordingly, the X-ray diagnostic apparatus 100 according to the first embodiment can generate the synthesized image matched with the display region of the display 23, and enables an image suitable for observation to be displayed.

Second Embodiment

Next, the following describes a second embodiment. The configuration of the X-ray diagnostic apparatus 100 according to the present embodiment is basically the same as the configuration of the X-ray diagnostic apparatus 100 illustrated in FIG. 1. Thus, the following mainly describes differences from the X-ray diagnostic apparatus 100 according to the first embodiment. A component having the same function as that of the component illustrated in FIG. 1 is denoted by the same reference numeral, and redundant description will not be repeated.

In the first embodiment described above, described is a case of displaying the synthesized image on a two-screen monitor (a monitor of a normal size). The second embodiment describes a case of displaying the synthesized image on a large-screen monitor.

Figure 7:
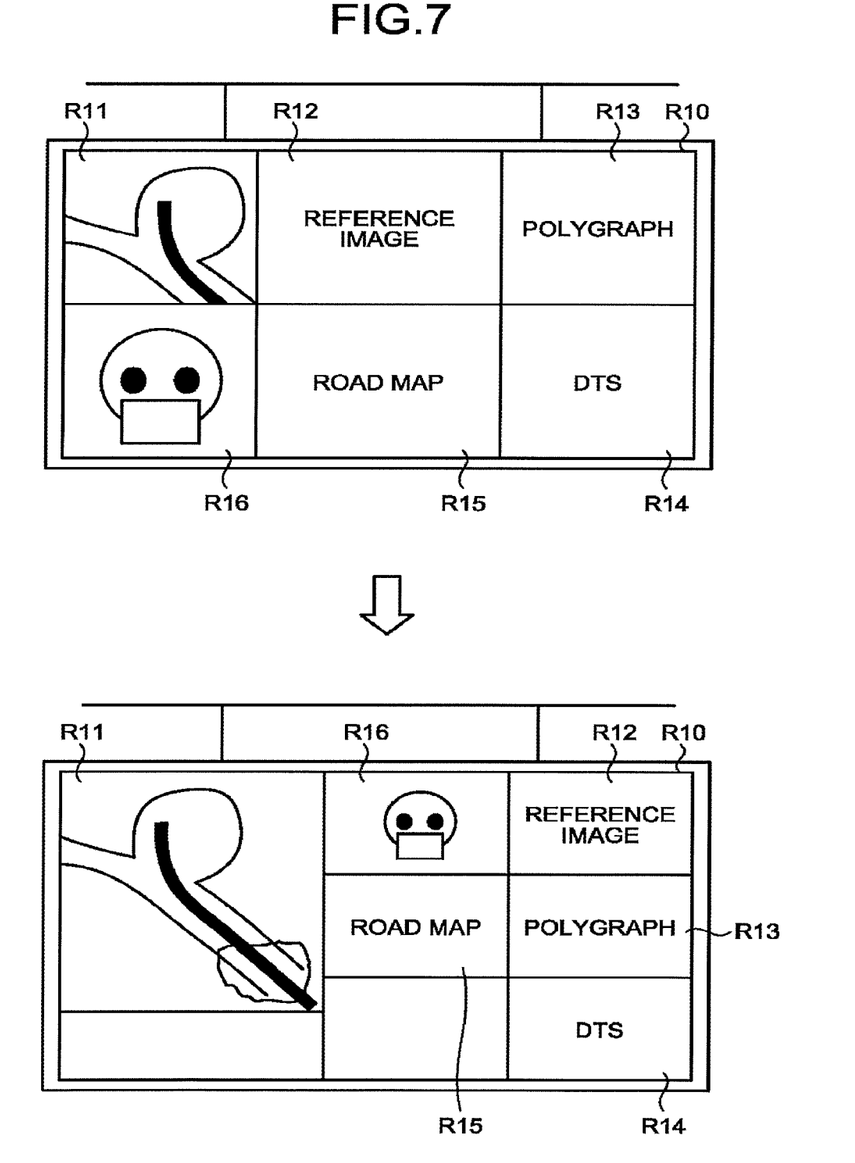
FIG. 7 is a diagram for explaining an example of processing performed by a control function according to a second embodiment.

The synthesizing function 211 according to the second embodiment determines the image size of the synthesized image in accordance with the X-ray irradiation region. In a case of displaying the synthesized image on the large-screen monitor, the control function 212 according to the second embodiment changes the display region of the synthesized image on the display 23. Specifically, the control function 212 changes the size of the display region of the synthesized image on the display 23 in accordance with the X-ray irradiation region, and displays the synthesized image generated by the synthesizing function 211 in the changed display region. FIG. 7 is a diagram for explaining an example of processing performed by the control function 212 according to the second embodiment. For example, as illustrated in the upper diagram of FIG. 7, the display 23 is a large screen, and an overall display region R10 includes a region R11 for displaying the synthesized image, a region R12 for displaying a reference image, a region R13 for displaying a polygraph, a region R14 for displaying a Dose Tracking System (DTS), a region R15 for displaying a road map, and a region R16 for displaying a photographed image.

For example, the control function 212 changes the size of the region R11 in accordance with the X-ray irradiation region. By way of example, the control function 212 magnifies the region R11 as illustrated in the lower diagram of FIG. 7. The control function 212 changes at least one of the size and the position of the display region for displaying a display target other than the synthesized image on the display 23 to change the size of the region R11 for the synthesized image, and causes the synthesized image to be displayed in the changed region R11. For example, as illustrated in the lower diagram of FIG. 7, the control function 212 reduces the size of the regions R12 to R16 and changes placement thereof to secure a space for magnifying the region R11, and magnifies the region R11 utilizing the secured space.

The synthesizing function 211 generates the synthesized image matched with the size of the region R11 magnified by the control function 212. For example, the synthesizing function 211 magnifies the first X-ray image I1 to be matched with the second X-ray image I2 while keeping the display size of the high-definition second X-ray image I2 as much as possible. That is, the control function 212 changes the size of the display region so that the size of the second X-ray image I2 on the display 23 is kept to be substantially constant. Accordingly, when the display 23 has a large screen, the control function 212 can cause the entire region of interest to be displayed while causing the high-definition second X-ray image I2 to be displayed larger. Thus, in changing the display region of the synthesized image, the control function 212 acquires the size of the first X-ray image and the second X-ray image from the X-ray irradiation region, and changes the size and the placement of the display region while displaying the acquired size to be maximum so that the region for the other display target is not smaller than a required size.

Figure 8:
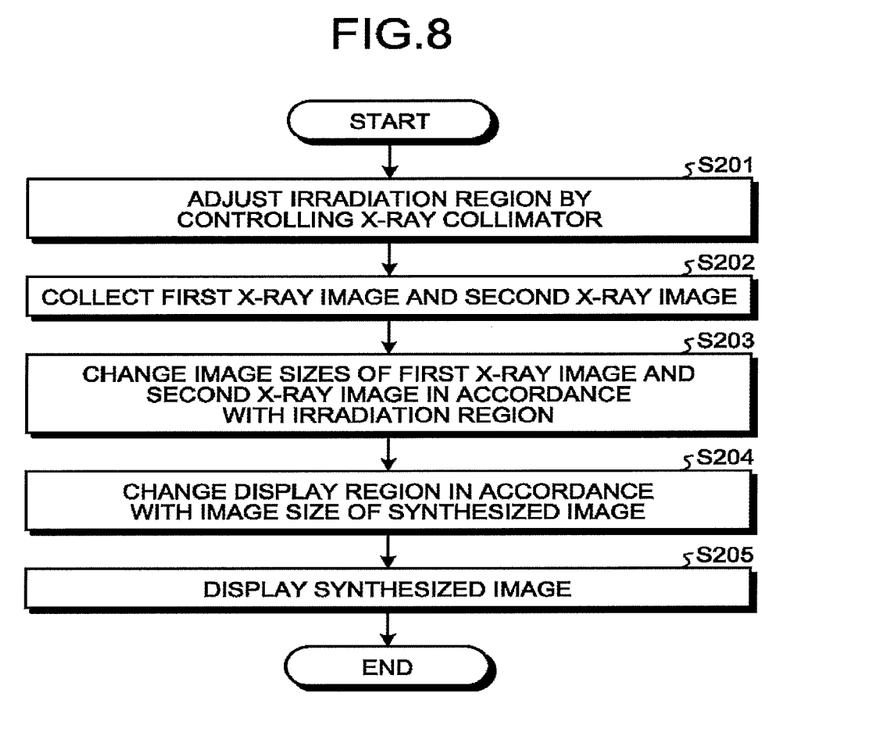
FIG. 8 is a flowchart illustrating a processing procedure of an X-ray diagnostic apparatus according to the second embodiment.

Next, the following describes processing performed by the X-ray diagnostic apparatus 100 according to the second embodiment with reference to FIG. 8. FIG. 8 is a flowchart illustrating a processing procedure of the X-ray diagnostic apparatus 100 according to the second embodiment. Steps S201, S202, S204, and S205 illustrated in FIG. 8 are steps at which the processing circuitry 21 reads out, from the storage 25, the program corresponding to the control function 212 to be executed. Step S203 is a step at which the processing circuitry 21 reads out, from the storage 25, the program corresponding to the synthesizing function 211 to be executed.

At Step S201, the processing circuitry 21 controls the X-ray collimator 13 to adjust the X-ray irradiation region. At Step S202, the processing circuitry 21 collects the first X-ray image and the second X-ray image. At Step S203, the processing circuitry 21 changes the image sizes of the first X-ray image and the second X-ray image in accordance with the X-ray irradiation region.

At Step S204, the processing circuitry 21 changes the display region of the display 23 in accordance with the image size of the synthesized image. At Step S205, the processing circuitry 21 causes the display 23 to display the generated synthesized image.

As described above, according to the second embodiment, the synthesizing function 211 determines the image size of the synthesized image in accordance with the irradiation region. The control function 212 changes the size of the display region of the synthesized image on the display 23 in accordance with the irradiation region, and causes the synthesized image generated by the synthesizing function 211 to be displayed in the changed display region. Accordingly, the X-ray diagnostic apparatus 100 according to the first embodiment enables the entire region of interest to be displayed while causing the high-definition second X-ray image I2 to be displayed larger.

According to the second embodiment, the control function 212 changes at least one of the size and the position of the display region for displaying a display target other than the synthesized image on the display 23 to change the size of the display region of the synthesized image, and causes the synthesized image to be displayed in the changed display region. Thus, the X-ray diagnostic apparatus 100 according to the first embodiment enables the synthesized image to be displayed in a larger region. As a result, the entire region of interest is enabled to be displayed larger while causing the high-definition second X-ray image I2 to be displayed larger.

Third Embodiment

The first and the second embodiments have been described above, but various different embodiments may be implemented in addition to the first and the second embodiments.

The components of the devices illustrated in the drawings of the first and the second embodiments are merely conceptual, and it is not required that it is physically configured as illustrated necessarily. That is, specific forms of distribution and integration of the devices are not limited to those illustrated in the drawings. All or part thereof may be functionally or physically distributed/integrated in arbitrary units depending on various loads or usage states. All or any part of processing functions executed by the respective devices may be implemented by a CPU and a program that is analyzed and executed by the CPU, or may be implemented as hardware using wired logic.

The display method described in the above embodiments can be implemented by executing the control program prepared in advance by a computer such as a personal computer and a workstation. The display program may be distributed via a network such as the Internet. The control program may be recorded in a computer-readable recording medium such as a hard disk, a flexible disk (FD), a CD-ROM, an MO, and a DVD, and may be executed by being read out from the recording medium by the computer.

As described above, according to at least one of the embodiments, efficiency of inspection can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
   an X-ray tube configured to radiate X-rays;
   an X-ray collimator configured to change an irradiation region of the X-rays radiated by the X-ray tube;
   an X-ray detector that includes a first detector and a second detector having a smaller detection area than a detection area of the first detector, and is configured to be able to detect the X-rays radiated to a fixed irradiation region, after being changed by the X-ray collimator, with the first detector and the second detector at the same time by arranging the first detector and the second detector so as to overlap in an irradiation direction of the X-rays and detecting the X-rays radiated to an overlapping region where the first detector and the second detector overlap with each other; and
   processing circuitry configured to
   generate a synthesized image obtained by synthesizing a first X-ray image generated based on an output from the first detector in the fixed irradiation region, and a second X-ray image generated based on an output from the second detector in the fixed irradiation region, the synthesized image having an image size corresponding to an aspect ratio of the fixed irradiation region, and cause a display to display the synthesized image.

2. The X-ray diagnostic apparatus according to claim 1, wherein the processing circuitry is configured to
   determine a side serving as a reference of the image size of the synthesized image in accordance with the aspect ratio of the fixed irradiation region, and
   generate the synthesized image obtained by synthesizing the first X-ray image and the second X-ray image with an image size corresponding to a length of the determined side.

3. The X-ray diagnostic apparatus according to claim 2, wherein the processing circuitry is configured to determine a long side of the fixed irradiation region to be a side serving as a reference of the image size.

4. The X-ray diagnostic apparatus according to claim 2, wherein the processing circuitry is configured to generate the synthesized image obtained by synthesizing the first X-ray image and the second X-ray image so that the length of the side serving as a reference of the image size of the synthesized image is matched with a length of a corresponding side of a display region of the synthesized image on the display.

5. The display method according to claim 2, comprising:
   generating the synthesized image obtained by synthesizing the first X-ray image and the second X-ray image so that the length of the side serving as a reference of the image size of the synthesized image is matched with a length of a corresponding side of a display region of the synthesized image on the display.

6. The X-ray diagnostic apparatus according to claim 1, wherein the second detector has a pixel size smaller than that of the first detector.

7. The X-ray diagnostic apparatus according to claim 1, wherein the processing circuitry is configured to sequentially acquire the first X-ray image and the second X-ray image, and sequentially generate the synthesized image based on the acquired first X-ray image and the acquired second X-ray image.

8. The display method according to claim 1, wherein the second detector has a pixel size smaller than that of the first detector.

9. The display method according to claim 1, comprising sequentially acquiring the first X-ray image and the second X-ray image, and sequentially generating the synthesized image based on the acquired first X-ray image and the acquired second X-ray image.

10. An X-ray diagnostic apparatus, comprising:
    an X-ray tube configured to radiate X-rays;
    an X-ray collimator configured to change an irradiation region of the X-rays radiated by the X-ray tube;
    an X-ray detector that includes a first detector and a second detector having a smaller detection area than a detection area of the first detector, and is configured to be able to detect the X-rays radiated to a fixed irradiation region, after being changed by the X-ray collimator, with the first detector and the second detector at the same time by arranging the first detector and the second detector so as to overlap in an irradiation direction of the X-rays and detecting the X-rays radiated to an overlapping region where the first detector and the second detector overlap with each other: and
    processing circuitry configured to
    generate a synthesized image obtained by synthesizing a first X-ray image generated based on an output from the first detector in the fixed irradiation region, and a second X-ray image generated based on an output from the second detector in the fixed irradiation region, and cause a display to display the synthesized image, wherein the processing circuitry is configured to
    change a size of a display region of the synthesized image on the display in accordance with the fixed irradiation region, and
    cause the synthesized image to be displayed in the changed display region.

11. The X-ray diagnostic apparatus according to claim 10, wherein the processing circuitry is configured to
    change at least one of a size and a position of the display region for displaying a display target other than the synthesized image on the display to change the size of the display region of the synthesized image, and
    cause the synthesized image to be displayed in the changed display region.

12. The X-ray diagnostic apparatus according to claim 10, wherein the processing circuitry is configured to change a size of the display region so that a size of an image obtained by the second detector is kept to be substantially constant on the display.

13. The X-ray diagnostic apparatus according to claim 10, wherein the second detector has a pixel size smaller than that of the first detector.

14. The X-ray diagnostic apparatus according to claim 10, wherein the processing circuitry is configured to sequentially acquire the first X-ray image and the second X-ray image, and sequentially generate the synthesized image based on the acquired first X-ray image and the acquired second X-ray image.

15. A display method for displaying an X-ray image generated based on an output from an X-ray detector that includes a first detector and a second detector having a smaller detection area than a detection area of the first detector, and is configured to be able to detect X-rays radiated to a fixed irradiation region, after being changed by an X-ray collimator for changing an irradiation region of the X-rays radiated by an X-ray tube, with the first detector and the second detector at the same time by arranging the first detector and the second detector so as to overlap in an irradiation direction of the X-rays and detecting the X- rays radiated to an overlapping region where the first detector and the second detector overlap with each other, the display method comprising:
    generating a synthesized image obtained by synthesizing a first X-ray image generated based on an output from the first detector in the fixed irradiation region, and a second X-ray image generated based on an output from the second detector in the fixed irradiation region, the synthesized image having an image size corresponding to an aspect ratio of the fixed irradiation region, and
    displaying the synthesized image on a display.

16. The display method according to claim 15, comprising:
    determining a side serving as a reference of the image size of the synthesized image in accordance with the aspect ratio of the fixed irradiation region, and
    generating the synthesized image obtained by synthesizing the first X-ray image and the second X-ray image with an image size corresponding to a length of the determined side.

17. The display method according to claim 16, comprising determining a long side of the fixed irradiation region to be a side serving as a reference of the image size.

* * * * *